(12) United States Patent
Johnson et al.

(10) Patent No.: US 6,453,929 B1
(45) Date of Patent: Sep. 24, 2002

(54) ROTARY WASH VALVE

(75) Inventors: James E. Johnson, Sebastotpol; Neil Picha, Petaluma; Jon Nichols, Forestville, all of CA (US)

(73) Assignee: Innovadyne Technologies, Inc., Rohnert Park, CA (US)

( * ) Notice: Subject to any disclaimer, the term of this patent is extended or adjusted under 35 U.S.C. 154(b) by 0 days.

(21) Appl. No.: 09/785,914

(22) Filed: Feb. 16, 2001

(51) Int. Cl.[7] .............................................. F16K 11/074
(52) U.S. Cl. ............... 137/15.05; 137/240; 137/625.11; 137/625.12
(58) Field of Search .......................... 137/240, 624.13, 137/624.14, 625.11, 625.12, 625.18, 625.46, 862, 887, 15.05; 251/208

(56) References Cited

U.S. PATENT DOCUMENTS

| | | | | |
|---|---|---|---|---|
| 835,928 A | * | 11/1906 | Allen ................. | 137/625.46 X |
| 1,023,903 A | * | 4/1912 | Weiss, Jr. .......... | 137/625.46 X |
| 1,760,902 A | * | 6/1930 | Grattan .................. | 137/624.13 |
| 2,974,681 A | * | 3/1961 | Whitehurst ........ | 137/625.11 X |
| 4,256,163 A | * | 3/1981 | Orszullok .............. | 137/625.31 |
| 5,954,092 A | * | 9/1999 | Kroutil et al. ......... | 137/624.13 |
| 6,012,488 A | | 1/2000 | Nichols | |

OTHER PUBLICATIONS

Rheodyne Part Numbers, Sheet of Sample Injection Valves Models 7010, 9010, and 3710/3710i, Apr. 1999.

* cited by examiner

Primary Examiner—John Rivell
(74) Attorney, Agent, or Firm—Beyer Weaver & Thomas

(57) ABSTRACT

A wash system for a fluid handling system that permits simultaneous washing of a plurality of parallel fluid channels is disclosed. In one aspect of the invention, a specialized rotary wash valve is described. In another aspect of the invention a system which incorporates wash and selector valves is described which permits a plurality of separate fluid lines emerging from the selector valve to be washed simultaneously.

15 Claims, 3 Drawing Sheets

CENTRAL WASH SYSTEM

CENTRAL WASH SYSTEM

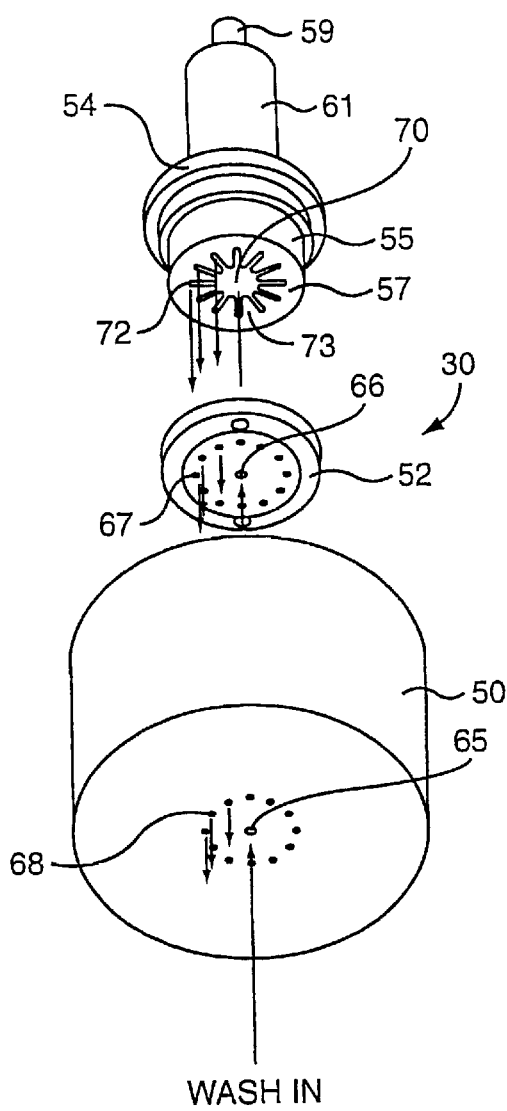
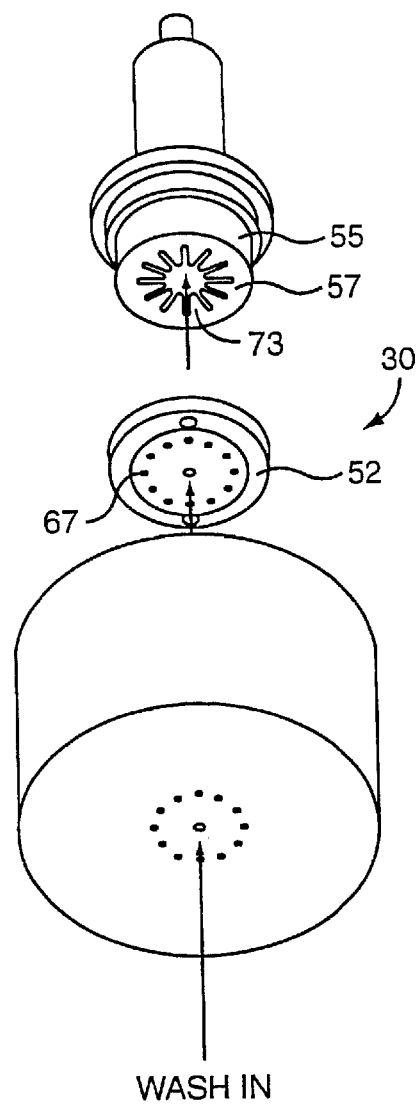
FIG. 2
FIG. 3
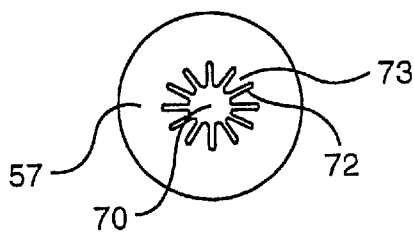
FIG. 4
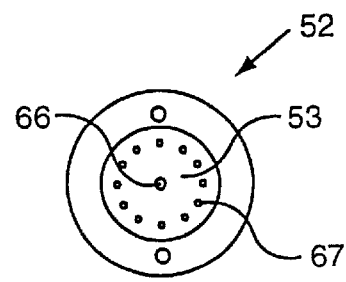
FIG. 5

ROTARY WASH VALVE

BACKGROUND OF THE INVENTION

The present inventions relate generally to rotary valve based fluid handling systems. More particularly, wash delivery systems that permit simultaneous washing of multiple output fluid paths from a rotary valve are described.

Recent advances in drug discovery have produced an overwhelming number of drug-like compounds to be tested for activity against protein targets. These drug-like compounds have various origins including natural products, and compounds produced through traditional organic syntheses and combinatorial syntheses. Typically, the drug-like compounds are archived in compound libraries at differing concentrations. Retrieval and dilution (e.g., normalization), of such compounds is generally performed with multiple precision metering devices attached to multiple distinct channels, with each channel being capable of independently performing a dilution. The precision metering devices are preferably capable of delivering very small (e.g. sub-microliter magnitude) precise amounts of the retrieved (and possibly diluted) compounds for testing.

In all liquid handling systems a cleansing of the fluid channels must be accomplished prior to the manipulation of the next compound. This cleansing can be achieved by washing the channels or, alternatively, by attaching a new disposable tip. Disposable tips are extremely expensive in the context of compound screening where an extensive library may contain as many as a million or more samples. Thus, washing the channels is generally preferred. However, the washing step can be a rate limiting factor in the liquid handling protocol. Accordingly, improved precision liquid handling systems that can incorporate simultaneous washing of a plurality of different fluid channels would be desirable.

SUMMARY OF THE INVENTION

To achieve the foregoing and other objectives, and in accordance with the purpose of the present invention, a wash system for a precision fluid handling system that permits simultaneous washing of a plurality of parallel fluid channels is disclosed. In one aspect of the invention, a specialized rotary wash valve is described. In another aspect of the invention a system that incorporates independent wash and selector valves which permits a plurality of separate fluid lines emerging from the selector valve to be washed simultaneously is described.

In one system aspect of the invention, independent wash and selector valves are utilized. The selector valve has a selector input port and a plurality of selector output ports. Each selector output port has an associated dispensing line. The selector valve has a number of different working positions which each make a fluidic connection between the selector input port and a particular one of the selector output ports. The wash valve has a wash fluid input port and a plurality of wash fluid output ports. Each wash output port has an associated wash line that is coupled to an associated dispensing line. In a first working position, the wash valve makes a fluidic connection between the wash fluid input port and the plurality of wash fluid output port. In a second working position the wash fluid input port is disconnected from the plurality of wash fluid output ports. With this arrangement, all of the dispensing lines may be washed in parallel by simply opening the wash valve.

In a preferred embodiment, both the wash valve and the selector valve are rotor based valves that have a rotor face plate that rotates relative to a stator face plate to make and decouple fluidic connections between their respective input and output ports.

In another aspect of the invention a unique rotary wash valve structure is described. In this embodiment the rotor face has a central recess and a multiplicity of angularly spaced grooves that extend radially outward from the central recess. The stator has a stator face that has a central passage that opens opposite the central recess of the rotor face and extends to the wash fluid input port. The stator also has a plurality of outer holes that each couple to an associated wash fluid output port. Each outer hole is aligned with an associated groove when the valve is disposed in a first position. The rotor face and stator are arranged such that when the valve is rotated to a second position, the outer holes do not have any fluidic connection with the grooves such that the outer holes are all substantially dead-headed at the rotor face. one embodiment, the only openings in the rotor face are the central recess and the multiplicity of grooves that extend radially outward from the central recess and the valve has just two operational positions.

BRIEF DESCRIPTION OF THE DRAWINGS

The invention, together with further objects and advantages thereof, may best be understood by reference to the following description taken in conjunction with the accompanying drawings in which:

FIG. 2 is an exploded perspective view of a wash valve in accordance with one embodiment of the present invention with the rotor face situated in the wash position.

FIG. 3 is an exploded perspective view of the wash valve of FIG. 2 with the rotor face situated in the off position.

FIG. 4 is a diagrammatic view of the rotor face of the wash valve illustrated in FIG. 2.

FIG. 5 is a diagrammatic view of the stator face of the wash valve illustrated in FIG. 2.

DESCRIPTION OF THE INVENTION

Figure 1:
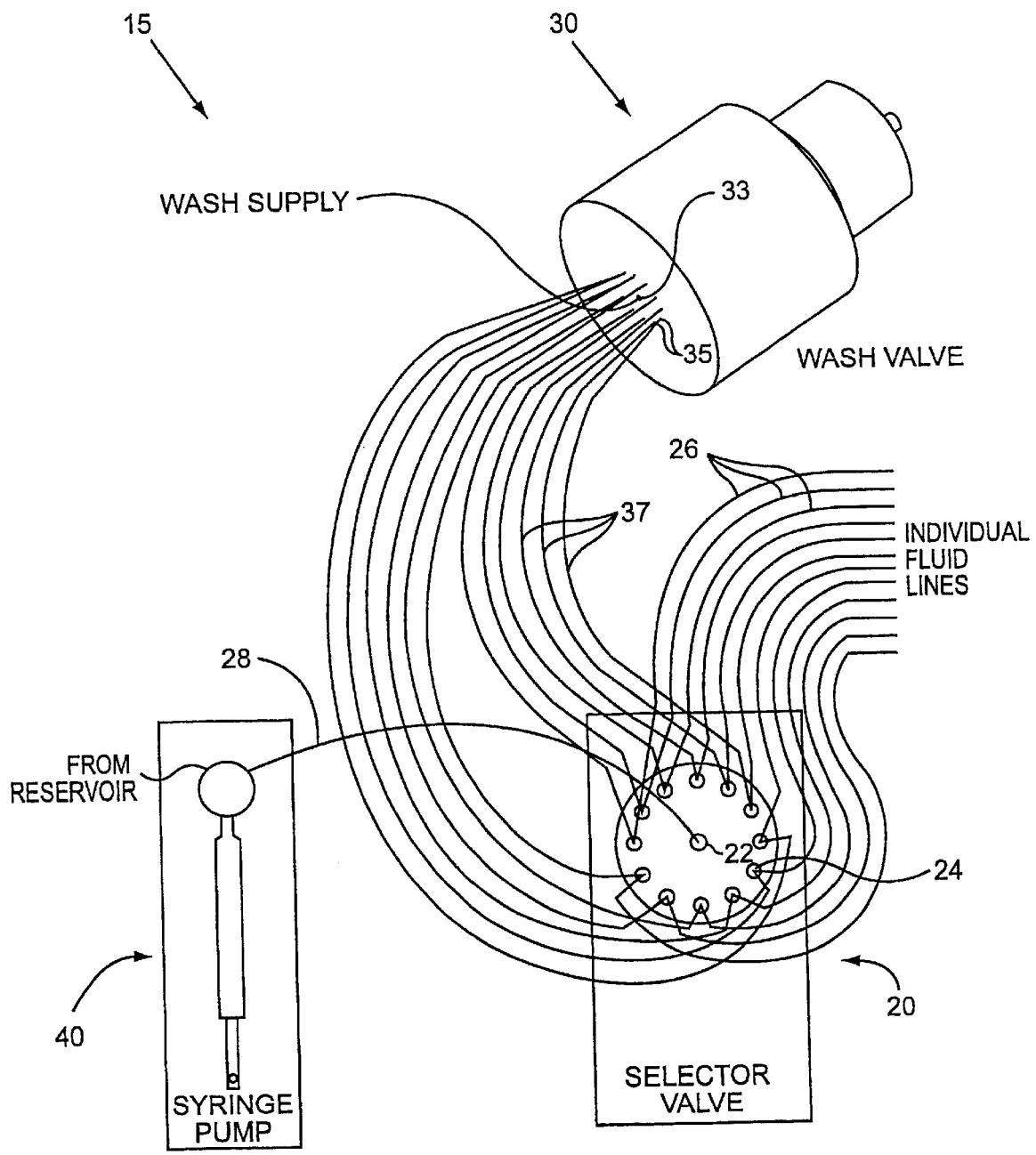
FIG. 1 is a schematic diagram of a fluid dispensing system that incorporates a parallel wash system in accordance with one embodiment of the present invention.

Referring initially to FIG. 1, a precision fluid delivery system 15 that is well adapted for delivering a number of very small precise amounts of liquid using a multiplicity of distinct parallel channels is illustrated. The precision fluid delivery system 15 is based on a multi-channel rotary selector valve 20 and includes a wash valve 30 and a metering system 40 that meters fluids delivered by the selector valve 20. For the purposes of illustration, a twelve-channel rotary selector valve 20 is shown. However, it should be apparent that the number of channels provided in the selector valve may be widely varied in accordance with the needs of a particular system. Rotary selector valves that are capable of delivering precise, very small volumes of liquid have been available for some time. By way of example, Rheodyne, Inc. of Rohnert Park Calif. produces a number of such rotary selector valves. One example is the RV350-106.

The rotary selector valve 20 has a selector input port 22 and a plurality of selector output ports 24. Each selector output port 24 has an associated dispensing line 26. The selector valve has a number of different working positions which each makes a fluidic connection between the selector input port 22 and a particular one of the selector output ports 24. In the embodiment shown, the selector valve 20 has twelve working positions, one for each output port 24. The input port 22 has an accompanying supply line 28 that is connected to a suitable metering device 40. In the embodiment shown, the metering device takes the form of a syringe pump 40, although as will be appreciated by those skilled in the art, any suitable metering device may be used. The use, control and operation of the selector valve 20 will not be described in detail herein since the selector valve may be operated in a wide variety of manners as will be well understood by those skilled in the art.

The wash valve 30 has a wash fluid input port 33 and a plurality of wash fluid output ports 35. Each wash output port 35 has an associated wash line 37 that is coupled to an associated dispensing line 26 (from the selector valve 20). In a first working position, the wash valve 30 makes a fluidic connection between the wash fluid input port 33 and the plurality of wash fluid output ports 35. In a second working position the wash fluid input port 33 is disconnected from the plurality of wash fluid output ports 35. This can readily be accomplished by deadheading the output ports as will be described in more detail below with respect to FIGS. 2 and 3. With this arrangement, all of the dispensing lines 26 may be washed in parallel by simply opening the wash valve 30.

Referring next to FIGS. 2 and 3, a representative rotary wash valve 30 will be described. The wash valve 30 includes a stator 50, an independent stator face plate 52 and a rotor 55 having a rotor face 57. The wash valve also includes a rotor housing 54 that couples to the stator 50, a drive shaft 59 that co-axially carries the rotor 55 and a drive system 61. The drive system (not shown in figures), which most commonly takes the form of a stepping motor, is provided to rotate the drive shaft and thus the rotor 55 relative to the stator face 52.

The stator 50 and stator face plate each have an aligned central input channel 65, 66 that is fed by the wash valve input port 33. They also include a plurality of aligned output channels 67, 68 that open into the wash valve output ports 35. In the embodiment shown, the stator 50 and stator face plate 52 are individually formed for ease of manufacturing. In alternative embodiments they could be integrally formed. The stator and/or stator face input and output channels can, in theory, be routed in any manner desired. In the embodiment shown, they take the form of simple straight channels that extend substantially perpendicular to the rotor face 57.

As best illustrated in FIG. 4, the rotor face 57 has a concentric central recess 70 and a plurality of angularly spaced radial channels or grooves 72 that extend radially outward from the central recess thereby forming landings or contact surfaces 73 between adjacent radial channels 72. As with almost all rotary valves of the type illustrated, the rotor face 57 rests flush against the stator face 53 and preferably forms a substantially leak proof seal. In the embodiment shown, the rotor face has twelve radial channels 72 to match the number of dispensing and wash lines. However, the actual number of radial channels provided in any particular wash valve will depend highly on the desired number of independent wash lines.

As described above, in a first working position, the wash valve 30 makes a fluidic connection between the wash fluid input port 33 and the plurality of wash fluid output ports 35. The wash fluid enters the stator input channels 65 through the fluid input port 33 and pass through the stator face input channel 66 into the central recess 70 in the rotor face 57. In the first working position, the radial channels 72 are all aligned with corresponding output channels 68 in the face 57. This makes a good fluidic connection between the wash fluid input port 33 and each of the fluid output ports 35.

In the second working position the rotor is rotated such that the stator face output channel 67 are deadheaded against the contact surfaces 73 in the rotor face 57. This effectively decouples the wash fluid input port 33 from all of the wash fluid output ports 35. Also, deadheading the wash valve allows the syringe pump to still accurately aspirate through the selector valve.

Figure 6:
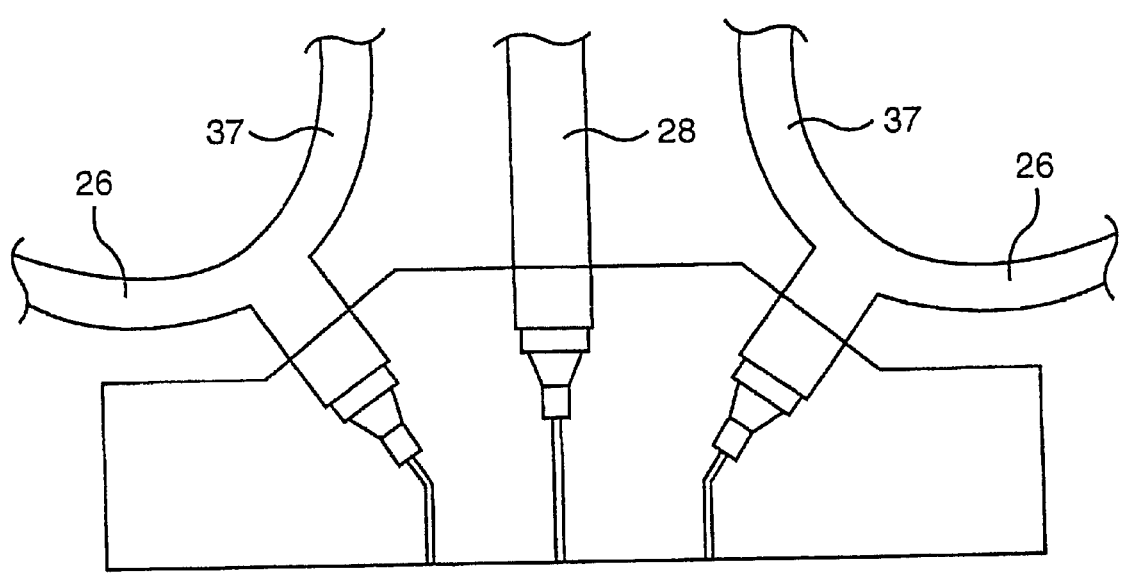
FIG. 6 is a diagrammatic cross sectional side view of a selector valve highlighting one suitable plumbing arrangement between the wash lines and fluid lines of FIG. 2.

Referring next to FIG. 6, a suitable arrangement for plumbing the wash lines 37 to the dispensing lines 26 will be described. In the embodiment shown, the wash lines 37 make a simple "T" or "Y" type connection 80 (or any other suitable connection) with the dispensing lines external to the selector valve. When the dispensing lines are being simultaneously washed, the selector valve is typically closed (although this is not an absolute requirement). Thus, in the washing mode, the wash fluid passes directly from the wash lines 37 to the dispensing lines 26, thereby simultaneously flushing all of the dispensing lines. In the embodiment shown, each wash line is connected to a single unique dispensing line. However, it should be appreciated that in some alternative embodiments, the wash lines 37 could be coupled to more than on dispensing line 26.

The described wash valve and/or wash system can be used in a wide variety of precision fluid delivery systems. In the context of the compound screening systems referred to in the background of this application, the described valve system architecture can provide an order of magnitude higher throughput for compound retrieval and dilution than most conventional delivery systems. This has the potential to facilitate significant improvements in the throughput of such compound screening systems.

Although only a few embodiments of the present invention have been described in detail, it should be understood that the present invention may be embodied in many other specific forms without departing from the spirit or scope of the invention. Although a particular wash valve construction has been illustrated and described, it should be appreciated that the geometry of the respective stator and rotor faces, the routing of the input and output lines within the stator/stator face, and the general construction of the rotary valve may all be widely varied without departing from the scope of the invention.

Further, the selector valve used within the described wash system, as well as the wash line plumbing into the selector valve can be widely varied. As suggested above, the plumbing between the wash lines and the dispensing lines can be external to the selector valve. Alternatively, the selector valve can be constructed to have internal washing capabilities and/or internal connections between the dispensing and wash lines. Therefore, the present examples are to be considered as illustrative and not restrictive, and the invention is not to be limited to the details given herein, but may be modified within the scope of the appended claims.

What is claimed is:

1. A fluid handling system comprising:
a selector valve having a selector input port and a plurality of selector output ports, the selector valve having a plurality of fluid delivery positions wherein in each fluid delivery position the selector valve makes a fluidic connection between the selector input port and a different one of the selector output ports;
a wash valve having a wash fluid input port and a plurality of wash fluid output ports, wherein the wash valve has a first position that makes a fluidic connection between the wash fluid input port and the plurality of wash fluid output ports, and a second position which disconnects the wash fluid input port from the plurality of wash fluid output ports;

a plurality of dispensing lines, each dispensing line being coupled to an associated one of the selector output ports; and a plurality of wash lines, each wash line coupling a selected one of the wash line output ports to an associated one of the dispensing lines to facilitate washing out the dispensing lines.

2. A system as recited in claim 1 wherein both the wash valve and the selector valve are rotor based valves that have a rotor face plate that rotates relative to a stator face plate to make and decouple fluidic connections between their respective input and output ports.

3. A system as recited in claim 1 wherein the wash valve further includes:

a rotor including a rotor face having a rotational axis, a central recess and a multiplicity of angularly spaced grooves that extend radially outward from the central recess;

a stator having a stator face that has a central passage that opens opposite the central recess of the rotor face and extends to the wash fluid input port, and a plurality of outer holes that each couple to an associated wash fluid output port, each outer hole being aligned with an associated groove when the rotor face is disposed in a first position, wherein the rotor face and stator are arranged such that when the rotor face is rotated to a second position relative to the stator, the outer holes do not have any fluidic connection with the grooves such that the outer holes are all substantially dead-headed at the rotor face.

4. A system as recited in claim 3 wherein:

the only openings in the rotor face are the central recess and the multiplicity of grooves that extend radially outward from the central recess; and the valve has just two operational positions.

5. A fluid handling system comprising:

a selector valve having a selector input port and two or more selector output ports, the selector valve having two or more fluid delivery positions wherein in each fluid delivery position the selector valve makes a fluidic connection between the selector input port and a different one of the selector output ports;

a wash valve having a wash fluid input port and a plurality of wash fluid output ports, wherein the wash valve has a first position in fluid flow communication between the wash fluid input port and the plurality of wash fluid output ports, and a second position out of fluid flow communication between the wash fluid input port from the plurality of wash fluid output ports;

two or more dispensing lines, each dispensing line being coupled to an associated one of the selector output ports; and a plurality of wash lines fluidly coupled to a selected one of the wash line outlet ports, wherein two or more of the plurality of wash lines coupling a selected one of the wash line outlet ports to an associated one of the two or more dispensing lines to facilitate washing out the dispensing lines.

6. A system as recited in claim 5 wherein, at least one of the wash valve and the selector valve is a rotor based valve.

7. A system as recited in claim 5, wherein the wash valve further includes:

a rotor including a rotor face having a rotational axis, a central recess and a multiplicity of angularly spaced grooves that extend radially outward from the central recess;

a stator having a stator face that has a central passage that opens opposite the central recess of the rotor face and extends to the wash fluid input port, and a plurality of outer holes that each couple to an associated wash fluid output port, each outer hole being aligned with an associated groove when the rotor face is disposed in the first position, wherein the rotor face and stator are arranged such that when the rotor face is rotated to the second position relative to the stator, the outer holes do not have any fluidic connection with the grooves such that the outer holes are all substantially dead-headed at the rotor face.

8. A system as recited in claim 7, wherein the only openings in the rotor face are the central recess and the multiplicity of grooves that extend radially outward from the central recess.

9. A system as recited in claim 7, wherein the valve has just two operational positions.

10. A system as recited in claim 7, wherein the stator includes an independent stator face plate that includes the stator face.

11. A system as recited in claim further comprising:

a drive shaft coupled to the rotor;

a drive motor for rotating the rotor relative to the stator; and a rotor housing that encases the drive motor.

12. If A method of flushing two or more dispensing lines coupled to associated selector outlet ports of a selector valve having two or more selector output ports, the selector valve further having two or more fluid delivery positions wherein in each fluid delivery position the selector valve makes a fluidic connection between the selector input port and a different one of the selector output ports, said method comprising;

positioning a wash valve in a first position to fluidly couple a wash fluid input port of the wash valve to a plurality of wash fluid output ports thereof, wherein two or more wash lines, each wash line coupling a selected one of the wash fluid output ports to an associated one of the two or more dispensing lines;

in the first position, flowing a washing fluid from the wash fluid input port to the wash fluid output ports, through the two or more wash lines and through the associated ones of the two or more dispensing lines to facilitate washing out the dispensing lines; and positioning the wash valve in a second position to fluidly de-couple the wash fluid input port of the wash valve from the plurality of wash fluid output ports thereof to prevent fluid communication between the wash fluid input port and the dispensing lines.

13. The method of claim 12, further including:

when the wash valve is positioned in the second position, flowing a dispensing fluid through the selector input port, the selected selector output port of the selector valve, and through the associated dispensing line thereof.

14. The method of claim 12, wherein
said wash valve is a rotor based valve having a rotor element and a stator element, and said positioning a wash valve in the first position includes rotating a rotor face of the rotor element relative a stator face of a stator element about a rotational axis to fluidly couple said wash fluid input port to the plurality of wash fluid output ports.

15. The method of claims wherein
said positioning the wash valve in a second position includes rotating the rotor face of the rotor element relative a stator face of a stator element about the rotational axis to fluidly decouple said wash fluid input port from the plurality of wash fluid output ports.

* * * * *